(12) United States Patent
Berg et al.

(10) Patent No.: US 7,450,730 B2
(45) Date of Patent: Nov. 11, 2008

(54) PERSONAL MONITORING SYSTEM FOR A USER AND METHOD FOR MONITORING A USER

(75) Inventors: Christian Berg, Uerikon (CH); Herbert Baechler, Meilen (CH)

(73) Assignee: Phonak AG, Staefa (CH)

( * ) Notice: Subject to any disclaimer, the term of this patent is extended or adjusted under 35 U.S.C. 154(b) by 820 days.

(21) Appl. No.: 11/019,612

(22) Filed: Dec. 23, 2004

(65) Prior Publication Data
US 2006/0140425 A1    Jun. 29, 2006

(51) Int. Cl.
    *H04R 25/00* (2006.01)
(52) U.S. Cl. .......................... 381/312; 381/315; 381/328
(58) Field of Classification Search ................. 381/312, 381/314, 315, 317, 323, 328, 57, 71.6, 72, 381/73.1, 74; 340/540; 128/864, 867; 181/129, 181/130, 135
See application file for complete search history.

(56) References Cited

U.S. PATENT DOCUMENTS

| | | | |
|---|---|---|---|
| 5,721,783 | A | 2/1998 | Anderson |
| 6,533,062 | B1 | 3/2003 | Widmer et al. |
| 6,661,901 | B1 | 12/2003 | Svean et al. |
| 6,895,098 | B2 * | 5/2005 | Allegro et al. ............... 381/312 |
| 7,072,480 | B2 * | 7/2006 | Rass .......................... 381/314 |
| 7,319,769 | B2 * | 1/2008 | Allegro-Baumann et al. ...... 381/312 |
| 2002/0080979 | A1 | 6/2002 | Brimhall et al. |
| 2003/0133583 | A1 | 7/2003 | Widmer et al. |

FOREIGN PATENT DOCUMENTS

| | | |
|---|---|---|
| EP | 1448 014 A1 | 8/2004 |
| WO | WO 01/82798 A1 | 11/2001 |

* cited by examiner

*Primary Examiner*—Huyen D Le
(74) *Attorney, Agent, or Firm*—David S. Safran

(57) ABSTRACT

The invention relates to a personal monitoring system for a user, comprising: at least one of a sensor (26, 28) for sensing an internal body parameter of the user and a sensor (14, 26, 28) for sensing an ambient parameter of the ambient around said user, an earpiece (10) for being worn at least in part in the ear canal of the user including an acoustic output transducer (18) for providing sound to the user's ear canal, an evaluation unit (22) communicating with the sensor, means (32, 34) for individually implementing an individually defined regulation for the sensed parameter into said evaluation unit, the evaluation unit being adapted for monitoring sensed values of the parameter over time and comparing them to the individually defined regulations for the sensed parameter and being adapted for continuously judging whether the sensed values of the parameter comply with the individual regulation or not, and a compliance control unit (24) communicating with the evaluation unit and with the output transducer for providing acoustic signals to the user's ear via the output transducer for providing the user with acoustic information regarding the present compliance of the sensed parameter with the implemented individual regulations depending on the judgement made by the evaluation unit.

47 Claims, 2 Drawing Sheets

PERSONAL MONITORING SYSTEM FOR A USER AND METHOD FOR MONITORING A USER

BACKGROUND OF THE INVENTION

1. Field of the Invention

The invention relates to a personal monitoring system for a user comprising a sensor for sensing an internal body parameter of the user and/or a sensor for sensing an ambient parameter of the ambience around the user, an earpiece for being worn at least in part in the user's ear canal including an acoustic output transducer for providing sound to the user's ear canal, an evaluation unit and a compliance control unit for providing the user with acoustic information regarding compliance of the sensed parameter with regulations. The invention further relates to a corresponding monitoring method.

2. Description of Related Art

U.S. Pat. No. 6,661,901 B1 relates to an active hearing protection device comprising an earplug with a customized shell wherein, in addition to the outer microphone for sensing unattenuated ambient sound, the audio signal processing unit and the speaker adapted to provide sound signals to the user's ear canal, an inner microphone is provided which is adapted to sense the sound level prevailing within the user's ear canal when wearing the hearing protection earplug, i.e. the inner microphone is provided for in-situ measurement of the actual sound exposure experienced by the user's ear. The earplug includes a noise exposure dosimeter function, according to which a stationary or semi-stationary noise dose is obtained by A-weighing the signal provided by the inner microphone and accumulating the squared values. Peak values are obtained by C-weighing the signal of the inner microphone and saving the peak values. The noise dose and the peak values are compared to predetermined limits and, if the limits are exceeded, an audible information is given via the speaker included within the earplug, to the user in form of warning signals or synthetic speech.

U.S. Pat. No. 5,721,783 relates to a system comprising an earpiece to be worn in the user's ear canal which is adapted for wireless communication with a remote processor unit which may be worn under the user's clothing. The earpiece comprises a microphone for sensing ambient sounds, an audio signal processing unit and a speaker for providing sound signals to the user's ear canal. The remote processor unit may be connected to sensors and peripheral devices which may provide information regarding body temperature, heart pulse or blood sugar level of the user by measuring the corresponding parameters, wherein the information obtained thereby is provided to the user in the form of audio signals via the speaker of the earpiece, such as by synthetic speech. In addition, external sensors communicating with the remote processor unit may be used for obtaining user location information or for detecting nuclear, biological and chemical weapons or for detecting metal parts. The obtained information is provided to the user by appropriate verbal warnings or distinctive alerting tones generated by the remote processor unit and sent to the earpiece for perception as audio signals by the user.

It is an object of the invention to provide for a personal monitoring system for a user regarding internal body parameters of the user and/or parameters of the ambience to which the user is exposed, wherein the system should be particularly well adapted to the individual needs of the user and wherein the user should be provided with efficient feedback from the system regarding the monitoring results. It is a further object of the invention to provide for a corresponding personal monitoring method.

SUMMARY OF THE INVENTION

These objects are achieved by a monitoring system as defined in claim 1 and a monitoring method as defined in claim 22.

The invention is beneficial in that, by individually implementing an individually defined regulation for the sensed parameter(s) into an evaluation unit, highly individual monitoring, i.e. monitoring specifically adapted to the individual needs of the user, is enabled. By providing the user with acoustic information regarding the compliance of the sensed parameter(s) with the implemented individual regulations via an acoustic output transducer provided in an earpiece worn by the user, feedback regarding the results of the monitoring is provided to the user in an efficient and reliable manner, without other persons being disturbed by sound signals provided by the monitoring system.

Preferably, the earpiece is a hearing protection device providing for a mechanical acoustic attenuation of at least 10 dB averaged over the audible frequency range when worn by the user. To this end, the earpiece may comprise a customized shell, i.e. a shell having an outer surface individually shaped according to the measured inner shape of the user's outer ear and ear canal. Preferably, the shell has an elasticity from shore D85 to shore D65 and may be made of polyamide. Preferably, the shell is produced by an additive layer-by-layer build-up process, such as layer-by-layer laser sintering of a polyamide powder.

According to one embodiment, the sensor is a microphone located at the outer side of the earpiece for sensing the ambient sound exposure experienced by the user. In this case, the earpiece may further include an audio signal processing unit for processing audio signals provided by the microphone as input to the output transducer, whereby an active hearing protection device can be realized. In this respect, the audio signal processing unit may be designed to modify the amplification and frequency shaping of the processed audio signals according to the level and frequencies of the sensed ambient sound. In order to monitor the sound exposure experienced by the user, the evaluation unit is adapted to determine separate sound levels for a plurality of frequency bands over time, wherein the individually defined regulation includes for each of the frequency bands a sound level threshold value and an alarm limit for an accumulated time period during which the respective sound level threshold value is exceeded. The individually defined regulation may depend on the acoustic attenuation performance of the earpiece.

Further, the individually defined regulation may include for each of the sound frequency bands a recovery limit for the respective accumulated time period during which the respective sound level threshold value is not exceeded. The individually defined regulation may further include for each of the frequency bands a plurality of sound level ranges and associated alarm limits for the respective accumulated time period during which the sensed sound level falls within the respective sound level range. Also in this case, the individually defined regulation may include for each of the sound level ranges a recovery limit for the respective accumulated time period during which the sensed sound level does not fall within the respective sound level range. If recovery limits are defined, the evaluation unit judges that the individually defined regulation is not complied with if at least one of the alarm time interval limits is exceed without the respective recovery time interval limit having been reached.

If the earpiece is designed as an active hearing protection device, the amplification of the processed audio signals may be modified according to the judgement made by the evaluation unit.

The evaluation unit may be adapted to continuously classify the ambient sound regarding at least one parameter, such as pleasant/unpleasant impression to the user, in addition to sound level, by frequency analysis.

Alternatively or in addition to the sound exposure by the user, the system may sense and monitor one of the following parameters: air temperature, humidity, air pressure, thermal radiation, X-ray intensity, radioactivity, chemical air composition and air contamination. If the system senses and monitors an internal body parameter, this parameter may be body temperature, blood pressure and/or heart pulse rate. Preferably, in this case the individually defined regulation regarding this parameter is defined depending on the medication of the user. In addition, the individually defined regulation regarding this parameter may be defined depending on at least one sensed ambient parameter or on at least one additionally sensed internal body parameter. For example, the upper limit of the heart pulse may be defined depending on the sensed blood pressure of the user and depending on the sensed air temperature and air pressure.

In general, the sensor preferably will be integrated within the earpiece. This will be possible for most ambient parameters, while the sensing of internal body parameters in some cases may require an external sensor worn by the user. However, also for sensing ambient parameters it is possible to use an external sensor, for example, a sensor permanently installed at a facility. Preferably communication between the earpiece and the external sensor is wireless. Preferably, the earpiece includes means for producing speech signals, alarm signals or pre-defined sounds as the acoustic feedback signals provided to the user, wherein explicit speech instructions to the user depending on the judgement made by the evaluation unit are preferred in order to provide for a highly reliable feedback to the user. The individually defined regulation may be implemented in the system from a remote data input device via a detachable wired or wireless data connection with a data input interface provided at the earpiece.

Preferably, the evaluation unit and the compliance control unit are formed by a digital signal processing unit which is integrated within the earpiece.

These and further objects, features and advantages of the present invention will become apparent from the following description when taken in connection with the accompanying drawing which, for purposes of illustration only, show several embodiments in accordance with the present invention.

BRIEF DESCRIPTION OF THE DRAWINGS

FIG. 1 relates to a personal monitoring system for a user which is designed as a hearing protection earplug 10 comprising a shell 12 which is adapted to be worn at least in part in a user's ear canal, i.e. at least a distal portion of the shell is to be inserted into the outer part of the user's ear canal in order to provide for an acoustic attenuation of at least 10 dB averaged over the audible frequency range when the earplug is worn by the user, in order to protect the user from excessive levels of ambient sound. The earplug may comprise an acoustic filter for adjusting the desired total acoustic attenuation or for adjusting the frequency dependent acoustic attenuation.

The shell preferably is a hard shell having an elasticity from shore D85 to D65 and preferably is made of polyamide. In order to achieve optimized fit of the shell within the user's outer ear and ear canal, the shell preferably has an outer surface individually shaped according to the measured shape of the user's outer ear and ear canal, i.e. the shell preferably has an individually customized outer shape. The shape of the user's outer ear and ear canal may be determined by direct three-dimensional scanning of the ear canal and the concha or by producing an impression of the ear canal and the concha which subsequently undergoes scanning. The scanning process may be carried out optically, preferably by laser scanning.

The digital data obtained by the scanning process is then used to create the hard shell by an additive or incremental layer-by-layer build up process. Such processes are also known as "rapid prototyping". A preferred additive build-up process is a layer-by-layer laser sintering process of powder material, preferably polyamide powder. Such processes are also known as "selective laser sintering" (SLS). The basic principle therein is the repeated deposition of a thin layer of material on a surface, with the desired sectional shape then being stabilized, i.e. hardened, by laser action. An overview regarding such processes can be found, for example, in US 2003/0133583 A1 or U.S. Pat. No. 6,533,062 B1.

Figure 1:
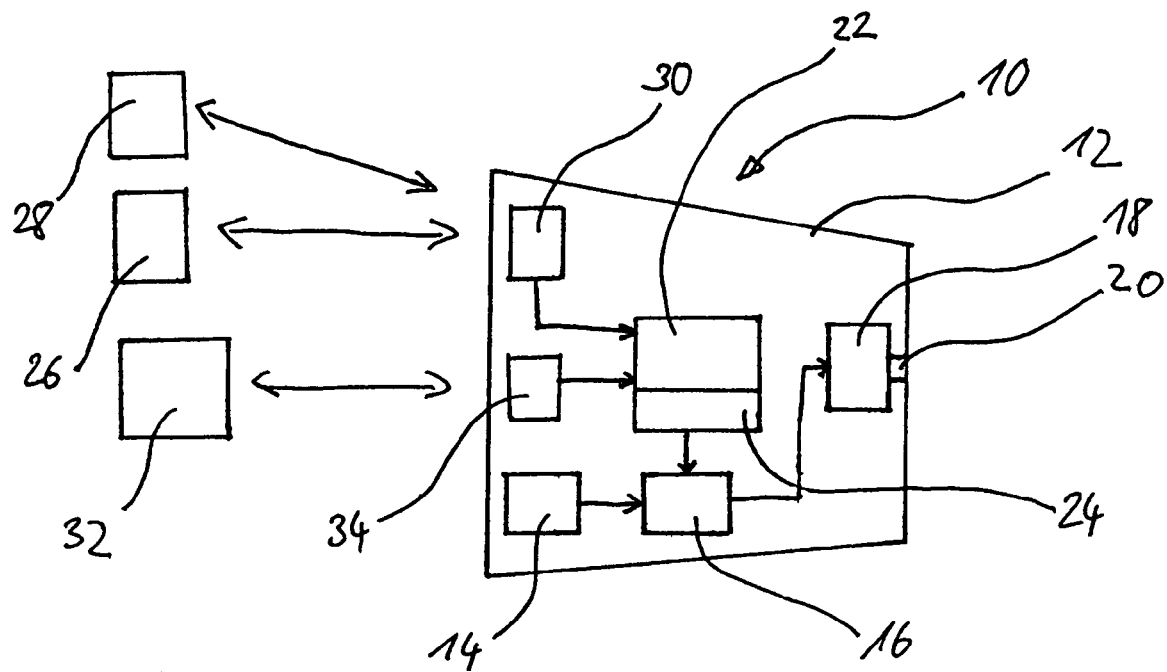
FIG. 1 shows a schematic view of a first embodiment of a monitoring system according to the invention.

The earplug 10 of FIG. 1 is provided with an active hearing protection function, i.e. the shell 12 comprises a microphone 14 for converting ambient sound into input audio signals, an audio signal processing unit 16 for processing the input audio signals into output audio signals and an acoustic output transducer (speaker) 18 which converts the output audio signal into sound provided at a sound outlet opening 20 at the distal end of the shell 12. Theses components are provided for allowing selected sound perception, such as speech signals, by the user even when wearing the earplug 10 in a noisy environment.

Further, the earplug 10 comprises an evaluation unit 22 and a compliance control unit 24. The evaluation unit 22 communicates with external sensors 26 and 28 via an interface 30. The interface 30 may be adapted for wireless communication with the sensors 26 and 28 or may serve to connect the sensors 26, 28 by a corresponding wire connection to the evaluation unit 22. The sensors 26, 28 may be designed for sensing an internal body parameter of the user, such as body temperature, blood pressure or heart pulse rate, and/or for sensing an ambient parameter of the ambient around the user, such as temperature, humidity, air pressure, thermal radiation, X-ray intensity, radio activity, chemical air composition and air contamination. The sensors 26, 28 may be adapted to be worn by the user or to be permanently installed at a facility.

The evaluation unit 22 is designed for monitoring values of the parameters sensed by the sensors 26, 28 over time and comparing them to individually defined regulations for these parameters. The evaluation unit 22 is further designed for continuously judging whether the sensed values of theses parameters comply with the respective individual regulation or not. The respective individual regulations for the sensed parameters are individually implemented into the evaluation unit 22 from an external data input device 32 via an interface 34 provided at the earplug 10. Data transfer between the data input device 32 and the interface 34 may occur in a wireless manner or via a detachable wire data connection.

The compliance control unit 24 communicates with the evaluation unit 22 and is designed for providing acoustic signals to the user's ear via the speaker 18 in order to provide the user with acoustic information regarding the present compliance of the sensed parameters with the corresponding implemented individual regulations depending on the judgement made by the evaluation unit 22. To this end, the compliance control unit 24 is connected to the audio signal processing unit 16. The acoustic feedback provided to the user may be provided in the form of synthetic speech signals, alarm signals or pre-defined sounds. Preferably, the acoustic feedback is provided in the form of explicit speech instructions to the user depending on the judgement made by the evaluation unit 22.

The individual regulation implemented in the evaluation unit 22 could be, for example an individual prescription from a physician (for example, the prescription to avoid excessive physical activity if temperature, altitude and/or humidity are above certain limits) or working environment regulations (for example, the regulation to work only a given number of hours per day if the temperature is above a given limit, the regulation to refrain from working if radioactivity or air contamination is above a given limit, etc.). The individual regulation may be defined depending on the medication of the user. The individual regulation for a body parameter may depend on the value of at least one other sensed parameter, such as a further body parameter or an ambient parameter. This also applies to the case where the individual regulation relates to an ambient parameter.

Figure 2:
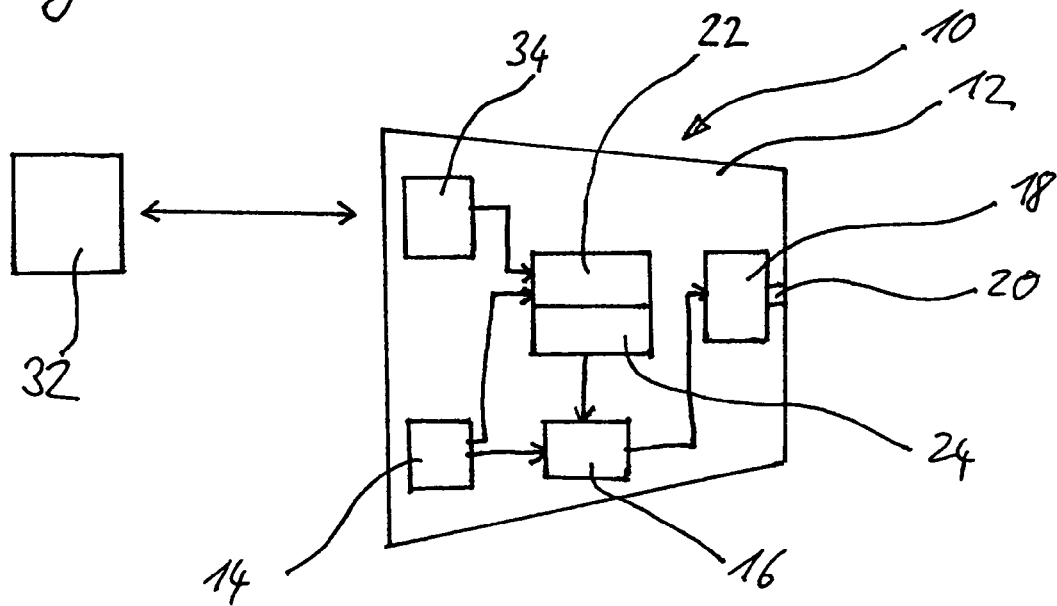
FIG. 2 shows a view like FIG. 1 of a second embodiment.

FIG. 2 relates to an embodiment in which a sensor is integrated within the earplug 10. In the example shown in FIG. 2 the sensor is a microphone 14, which serves two functions: On the one hand, the microphone 14 is provided, similarly to the embodiment of FIG. 1, for providing the hearing protection earplug 10 with an active hearing protection function via the audio signal processing unit 16 and the speaker 18; on the other hand, the microphone 14 serves to continuously measure the ambient sound exposure of the user wearing the earplug 10. To this end, the microphone 14 is not only connected with the audio signal processing unit 16 but also with the evaluation unit 22. As in the embodiment of FIG. 1, the evaluation unit 22 in addition is connected to the interface 34 for allowing an individual regulation regarding the sound levels sensed by the microphone 14 to be implemented via the external data input device 32.

The embodiment of FIG. 2 may serve to provide for a hearing protection ear plug 10 with a noise exposure control function, i.e. a dosimeter function. To this end, the evaluation unit 22 may be designed to determine separate sound levels for a plurality of frequency bands over time. Further, the evaluation unit 22 may be designed to continuously classify the ambient sound regarding one additional parameter, such as pleasant/unpleasant impression to the user, by frequency analysis, wherein the individually defined regulation includes a condition for this additional parameter and this additional parameter is used in the judgement made by the evaluation unit 22.

Preferably, the individually defined regulation includes for each of the frequency bands a sound level threshold value and an alarm limit for an accumulated time period during which the respective sound level threshold value is exceeded. The individually defined regulation may depend on the acoustic attenuation performance of the earplug 10.

Further, the individually defined regulation may include for each of the sound frequency bands a recovery limit for the respective accumulated time period during which the respective sound level threshold value is not exceeded. The individually defined regulation may further include for each of the frequency bands a plurality of sound level ranges and associated alarm limits for the respective accumulated time period during which the sensed sound level falls within the respective sound level range. Also in this case, the individually defined regulation may include for each of the sound level ranges a recovery limit for the respective accumulated time period during which the sensed sound level does not fall within the respective sound level range. If recovery limits are defined, the evaluation unit 22 judges that the individually defined regulation is not complied with if at least one of the alarm time interval limits is exceed without the respective recovery time interval limit having been reached.

The amplification of the audio signals processed by the audio signal processing unit 16 may be modified according to the judgement made by the evaluation unit 22.

Figure 3:
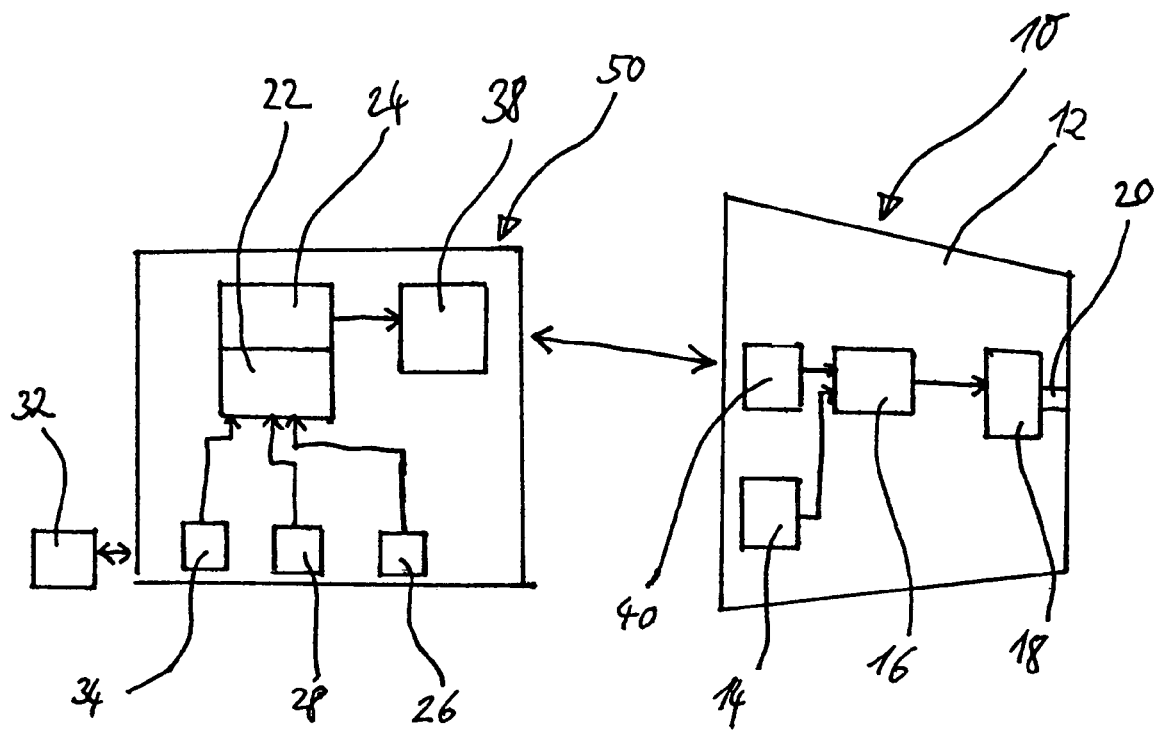
FIG. 3 shows a view like FIG. 1 of a third embodiment.

In FIG. 3 a modified embodiment is shown, wherein the evaluation unit 22 and the compliance control unit 24 are not integrated within the earplug 10 but rather are included in an external unit 50 which also includes the sensors 26, 28 of FIG. 1. The external unit 50 is provided with an interface 38 for communicating with an interface 40 provided at the earplug 10 in order to provide for acoustic feedback to the user via the speaker 18 of the earplug 10. Preferably, the communication between the earplug 10 and the external unit 50 occurs via a wireless connection; however, alternatively also a wire connection would be possible which preferably would be detachable.

The external unit 50 is provided with the interface 34 for allowing the individual regulation being implemented into the evaluation unit 22 from the external data input device 32.

Preferably, the external unit 50 is designed to be worn by the user.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as encompassed by the scope of the appended claims.

What is claimed is:

1. A personal monitoring system for a user, comprising: at least one of a sensor for sensing an internal body parameter of said user and a sensor for sensing an ambient parameter of the ambient around said user, an earpiece for being worn at least in part in an ear canal of said user including an acoustic output transducer for providing sound to said user's ear canal, an evaluation unit communicating with said sensor, means for individually implementing an individually defined regulation for said sensed parameter into said evaluation unit, said evaluation unit being adapted for monitoring sensed values of said parameter over time and comparing them to said individually defined regulations for said sensed parameter and being adapted for continuously judging whether said sensed values of said parameter comply with said individual regulation or not, and a compliance control unit communicating with said evaluation unit and with said output transducer for providing acoustic signals to a user's ear via said output transducer for providing said user with acoustic information regarding a present compliance of said sensed parameter with said implemented individual regulations depending on a judgement made by said evaluation unit.

2. The system of claim 1, wherein said earpiece is a hearing protection earplug providing for a mechanical acoustic attenuation of at least 10 dB averaged over an audible frequency range when worn by said user.

3. The system of claim 2, wherein said earpiece comprises a shell having an outer surface individually shaped according to a measured inner shape of said user's outer ear and ear canal.

4. The system of claim 3, wherein said shell is a hard shell with an elasticity of from shore D85 to shore D65.

5. The system of claim 1, wherein said sensor is a microphone located at an outer side of said earpiece for sensing an ambient sound exposure experienced by said user.

6. The system of claim 5, wherein said earpiece includes an audio signal processing unit for processing audio signals provided by said microphone as input to said output transducer.

7. The system of claim 6, wherein said audio signal processing unit is designed to modify an amplification and a frequency shaping of audio signals processed by said audio signal processing unit according to a level and frequencies of ambient sound sensed by said sensor.

8. The system of claim 5, wherein said evaluation unit is adapted to determine separate sound levels for a plurality of frequency bands over time.

9. The system of claim 5, wherein said evaluation unit 22) is adapted to continuously classify ambient sound regarding at least one parameter, in addition to sound level by frequency analysis.

10. The system of claim 1, wherein said sensor is adapted to sense one of the following ambient parameters: air temperature, humidity, air pressure, thermal radiation, X-ray intensity, radioactivity, chemical air composition and air contamination.

11. The system of claim 1, wherein said sensor is adapted to sense an internal body parameter selected from the group consisting of body temperature, blood pressure and heart pulse rate.

12. The system of claim 1, wherein said sensor is integrated within said earpiece.

13. The system of claim 1, wherein said sensor is an external sensor and wherein means are provided for establishing one of a wired and wireless communication connection between said earpiece and said external sensor.

14. The system of claim 13, wherein said sensor is adapted to be worn by said user.

15. The system of claim 13, wherein said sensor is adapted to be permanently installed at a facility.

16. The system of claim 1, wherein said earpiece includes means for producing at least one of speech signals, alarm signals and pre-defined sounds as said acoustic signals to be provided to said user.

17. The system of claim 16, wherein said acoustic signals include explicit speech instructions to said user depending on a judgement made by said evaluation unit.

18. The system of claim 1, wherein said means for individually implementing said individually defined regulation include a remote data input device and a data input interface provided at said earpiece.

19. The system of claim 18, wherein said data input interface is adapted for establishing a detachable wired data connection with said remote data input device.

20. The system of claim 18, wherein said data input interface is adapted for establishing a wireless data connection with said remote data input device.

21. The system of claim 1, wherein said evaluation unit and said compliance control unit are formed by a digital signal processing unit, with said earpiece comprising said digital signal processing unit.

22. A method for monitoring a user, comprising:
sensing at least one of an internal body parameter of said user and an ambient parameter of the ambient around said user;
individually implementing an individually defined regulation for said sensed parameter into an evaluation unit;
monitoring, by said evaluation unit, sensed values of said parameter over time and comparing them to said individually defined regulations for said sensed parameter;
continuously judging, by said evaluation unit, whether said sensed values of said parameter comply with said individual regulation or not;
providing acoustic signals to a user's ear via an output transducer located in an earpiece worn at least in part in an ear canal of said user for providing said user with acoustic feedback regarding a present compliance of said sensed parameter with said implemented individual regulation depending on a judgement made by said evaluation unit.

23. The method of claim 22, wherein said sensed ambient parameter is an ambient sound exposure experienced by said user, with ambient sound being converted into audio signals by a microphone provided at said earpiece.

24. The method of claim 23, further comprising processing said audio signals as input to said output transducer.

25. The method of claim 24, further comprising modifying an amplification of said processed audio signals according to a level and frequencies of sensed ambient sound.

26. The method of claim 24 further comprising modifying an amplification of said processed audio signals according to a judgement made by said evaluation unit.

27. The method of claim 23, further comprising determining, by said evaluation unit, separate sound levels for a plurality of frequency bands over time.

28. The method of claim 27, wherein said individually defined regulation includes for each of said frequency bands a sound level threshold value and an alarm limit for an accumulated time period during which a respective sound level threshold value is exceeded.

29. The method of claim 28, wherein said individually defined regulation includes for each of said sound frequency bands a recovery limit for a respective accumulated time period during which a respective sound level threshold value is not exceeded.

30. The method of claim 29, wherein said individually defined regulation includes for each of said frequency bands a plurality of sound level ranges and associated alarm limits for a respective accumulated time period during which a sensed sound level falls within a respective sound level range.

31. The method of claim 30, wherein said individually defined regulation includes for each of said sound level ranges a recovery limit for a respective accumulated time period during which a sensed sound level does not fall within a respective sound level range.

32. The method of claim 29, wherein said evaluation unit judges that said individually defined regulation is not complied with if at least one of said alarm limits is exceeded without a respective recovery limit having been reached.

33. The method of claim 23, further comprising continuously classifying, by said evaluation unit, ambient sound regarding at least one parameter, in addition to sound level, by frequency analysis, wherein said individually defined regulation includes a condition for said additional parameter and said additional parameter is used in a judgement made by said evaluation unit.

34. The method of claim 22, wherein said earpiece is worn in a manner as to provide for a mechanical acoustic attenuation of at least 10 dB averaged over an audible frequency range.

35. The method of claim 34, wherein said individually defined regulation depends on an acoustic attenuation performance of said earpiece.

36. The method of claim 22, wherein said sensor is integrated within said earpiece.

37. The method of claim 22, further comprising establishing one of a wired and wireless communication connection between said earpiece and an external sensor for sensing said parameter.

38. The method of claim 37, wherein said external sensor is worn by said user.

39. The method of claim 37, wherein said external sensor is permanently installed at a facility.

40. The method of claim 22, wherein said acoustic signals provided to said user's ear include speech signals.

41. The method of claim 40, wherein said acoustic signals provided to said user's ear include explicit instructions to said user depending on a judgement made by said evaluation unit.

42. The method of claim 22, wherein said sensed ambient parameter is one of air temperature, humidity, air pressure, thermal radiation, X-ray intensity, radioactivity, chemical air composition and air contamination.

43. The method of claim 22, wherein said internal body parameter is one of body temperature, blood pressure and heart pulse rate.

44. The method of claim 22, wherein said individually defined regulation is defined depending on a medication of said user.

45. The method of claim 22, wherein said individually defined regulation is defined depending on at least one sensed ambient parameter.

46. The method of claim 22, wherein said individually defined regulation is defined depending on at least one sensed internal body parameter.

47. The method of claim 22, further comprising establishing one of a detachable wired data connection and a wireless data connection with a remote data input device for individually implementing said individually defined regulation.

* * * * *